United States Patent
Li et al.

(10) Patent No.: US 10,626,455 B2
(45) Date of Patent: Apr. 21, 2020

(54) MULTI-PASS SEQUENCING

(71) Applicants: BGI Shenzhen, Shenzhen (CN); BGI Shenzhen Co., Ltd., Shenzhen (CN)

(72) Inventors: Handong Li, San Jose, CA (US); Y. Tom Tang, Saratoga, CA (US); Jing Yu, Shenzhen (CN); Hui Jiang, Shenzhen (CN); Wenwei Zhang, Shenzhen (CN); Guangyi Fan, Shenzhen (CN); He Zhang, Shenzhen (CN); Kailong Ma, Shenzhen (CN); Chunyu Geng, Shenzhen (CN)

(73) Assignees: BGI Shenzhen (CN); BGI Shenzhen Co., Ltd. (CN)

( * ) Notice: Subject to any disclaimer, the term of this patent is extended or adjusted under 35 U.S.C. 154(b) by 173 days.

(21) Appl. No.: 15/525,253

(22) PCT Filed: Nov. 10, 2015

(86) PCT No.: PCT/US2015/059903
§ 371 (c)(1),
(2) Date: May 8, 2017

(87) PCT Pub. No.: WO2016/077313
PCT Pub. Date: May 19, 2016

(65) Prior Publication Data
US 2018/0282800 A1    Oct. 4, 2018

Related U.S. Application Data

(60) Provisional application No. 62/078,306, filed on Nov. 11, 2014.

(51) Int. Cl.
*C12Q 1/6869* (2018.01)
*G01N 27/447* (2006.01)
*G01N 33/487* (2006.01)

(52) U.S. Cl.
CPC ..... *C12Q 1/6869* (2013.01); *G01N 27/44791* (2013.01); *G01N 33/48721* (2013.01)

(58) Field of Classification Search
None
See application file for complete search history.

(56) References Cited

U.S. PATENT DOCUMENTS

| | | | |
|---|---|---|---|
| 8,153,375 B2 | 4/2012 | Travers et al. | |
| 9,732,383 B2 | 8/2017 | Christians et al. | |
| 2012/0316075 A1 | 12/2012 | Buzby et al. | |
| 2013/0040827 A1* | 2/2013 | Macevicz | C12Q 1/6869 506/2 |
| 2013/0296173 A1* | 11/2013 | Callow et al. | C12Q 1/6874 506/2 |
| 2014/0061048 A1* | 3/2014 | Turner et al. | C12Q 1/6869 204/451 |
| 2014/0235461 A1 | 8/2014 | Yin et al. | |

FOREIGN PATENT DOCUMENTS

| | | | |
|---|---|---|---|
| EP | 1 225 234 A2 | 7/2002 | |
| WO | 2006/095169 A1 | 9/2006 | |
| WO | WO-2006095169 A1 * | 9/2006 | ........... C12Q 1/6813 |
| WO | 2013/185137 A1 | 12/2013 | |
| WO | 2014153625 | 10/2014 | |

OTHER PUBLICATIONS

PCT/US2015/059903, "International Search Report and Written Opinion", dated Feb. 16, 2016, 9 pages.
Cherf, G. et al. "Automated Forward and Reverse Ratcheting of DNA in a Nanopore at 5-Angstrom Precision." *Nature Biotechnology*, vol. 30, No. 4. Published Feb. 14, 2012. pp. 344-348.
Timp, W. et al. "DNA Base-Calling from a Nanopore Using a Viterbi Algorithm." *Biophysical Journal*, vol. 102, No. 10. Published May 12, 2012. pp. 37-39.
Drmanac, R. et al. "Human Genome Sequencing Using Unchained Base Reads on Self-Assembling DNA Nanoarrays." *Science*, vol. 327. Published Jan. 1, 2010. 5 pages.
Eid, J. et al. "Real Time DNA Sequencing from Single Polymerase Molecules." *Science*, vol. 323. Published Jan. 2, 2009. 7 pages.
Lou, D. et al. "High-Throughput DNA Sequencing Errors are Reduced by Orders of Magnitude Using Circle Sequencing." *Proceedings of the National Academy of Sciences*, vol. 110, No. 49. Published Dec. 3, 2013. 6 pages.
Travers, K. et al. "A Flexible and Efficient Template Format for Circular Consensus Sequencing and SNP Detection." *Nucleic Acids Research*, vol. 38, No. 15. Published Jun. 22, 2010. 8 pages.

* cited by examiner

*Primary Examiner* — Kaijiang Zhang
(74) *Attorney, Agent, or Firm* — Kilpatrick Townsend & Stockton LLP

(57) ABSTRACT

Improved single molecule sequencing methods, compositions, and devices, are provided. In a first aspect, the present invention provides a multi-pass method of sequencing a target sequence using nanopore sequencing, the method comprising: i) providing a non-naturally occurring concatemer nucleic acid molecule comprising a plurality of copies of the target sequence; ii) nanopore sequencing at least three copies of the target sequence in the concatemer, thereby obtaining a multi-pass sequence dataset, wherein the multi-pass sequence dataset comprises target sequence datasets for the at least three copies of the target sequence; and iii) using the multi-pass sequence dataset to determine the target sequence.

17 Claims, No Drawings
Specification includes a Sequence Listing.

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: synthetic sync sequence

<400> SEQUENCE: 1
agagagagag agagagagag                                              20

<210> SEQ ID NO 2
<211> LENGTH: 12
<212> TYPE: DNA
<213> ORGANISM: Artificial Sequence
<220> FEATURE:
<223> OTHER INFORMATION: synthetic sync sequence

<400> SEQUENCE: 2
atgatgatga tg                                                      12

<210> SEQ ID NO 3
<211> LENGTH: 9
<212> TYPE: DNA
<213> ORGANISM: Artificial Sequence
<220> FEATURE:
<223> OTHER INFORMATION: synthetic sync sequence

<400> SEQUENCE: 3 cagcagcag                                                           9
```

MULTI-PASS SEQUENCING

CROSS-REFERENCE TO RELATED APPLICATION

This application is a U.S. National Stage of PCT Application No. PCT/US2015/059903, filed Nov. 10, 2015, which claims the benefit of, and priority to, U.S. Provisional Application No. 62/078,306, filed Nov. 11, 2014, the contents of which are hereby incorporated by reference in the entirety for all purposes.

BACKGROUND OF THE INVENTION

Single molecule sequencing (SMS) methods, such as nanopore sequencing, have certain advantages over other next generation sequencing approaches. In particular, SMS is rapid and produces long read lengths. However, conventional SMS methods are characterized by a high error rate in raw reads. Error rate can be presented as a % error, corresponding to the number of errors per 100 called bases. Alternatively, error rate can be presented as a "Q" value. "Q," can be calculated using the following formula: −10× $\log_{10}(P)$, where P is the probability of an incorrect base call. See, Ewing & Green, 1998, *Genome Res.* 8:186-194. For example, Q10 refers to a 1 in 10 probability of an error, or a 90% accuracy, and Q30 refers to a 1 in 1000 probability of an error, or a 99.9% accuracy. Nanopore sequencing has been reported to provide a base-call accuracy in the range of only Q5 to Q7 (about 70-85%). Other SMS methods (e.g., zero-mode waveguide sequencing; SMRT Pacific Biosciences) also suffer from high error rates.

Nanopores and methods of sequencing using nanopores are known in the art. See, e.g., Clarke et al., 2009, "Continuous base identification for single-molecule nanopore DNA sequencing," *Nature Nanotechnology* 4:265-70; Riehnet et al., 2007, "Nanochannels for Genomic DNA Analysis: The Long and the Short of It" in *Integrated Biochips for DNA Analysis.* Springer NewYork, 151-186; Min et al., 2011, "Fast DNA sequencing with a graphene-based nanochannel device." *Nature Nanotechnology* 6.3:162-65; U.S. Pat. Nos. 6,673,615; 7,258,838; 7,238,485; 7,189,503; 6,627,067; 6,464,842; and 6,267,872; U.S. Patent Application Publication Nos. 2008/0248561, 2008/0171316, and 2008/0102504; and International Patent Application Publication No. WO 2014/096830, each of which is incorporated herein by reference. Most often, sequence is determined for one single-stranded DNA as it is translated through the nanopore. Both strands of a double-stranded polynucleotide can be sequenced by introducing a hairpin loop at one end of the double-stranded molecule and sequencing the linked sense and antisense strands sequentially (see WO 2013/014451). Sequencing of a double-stranded DNA as it is translated through a nanopore has been suggested (see, Wendell et al., 2009, "Translocation of double-stranded DNA through membrane-adapted phi29 motor protein nanopores" *Nature Nanotechnology* 4:765-72). In some approaches RNA is sequenced.

Conventional nanopore sequencing is single-pass sequencing, i.e., a single molecule containing one copy of a target sequence is translated through a nanopore one time to generate "single pass sequence information." Different polynucleotides sharing the same target sequence (e.g., a genomic DNA fragment) may be sequenced by translation through separate nanopores in a multiple pore array to generate multiple reads. The multiple reads can then be used to generate a consensus sequence. A method for moving a polynucleotide in both directions though a nanopore has been proposed, such that the sequence of single molecules might be read in both directions (see Cherf et al., 2012, "Automated Forward and Reverse Ratcheting of DNA in a Nanopore at Five Angstrom Precision" *Nat Biotechnol.* 30:344-48). However, it is unclear whether any error reduction would result and there appear to be significant barriers to practical implementation of such a system.

Accordingly, improved sequencing methods are needed.

BRIEF SUMMARY OF THE INVENTION

In a first aspect, the present invention provides a multi-pass method of sequencing a target sequence using nanopore sequencing, the method comprising: i) providing a non-naturally occurring concatemer nucleic acid molecule comprising a plurality of copies of the target sequence; ii) nanopore sequencing at least three copies of the target sequence in the concatemer, thereby obtaining a multi-pass sequence dataset, wherein the multi-pass sequence dataset comprises target sequence datasets for the at least three copies of the target sequence; and iii) using the multi-pass sequence dataset to determine the target sequence.

In some embodiments, adjacent copies of the target sequence are separated by a non-target sync sequence with a predetermined sequence and the nanopore sequencing further comprises sequencing at least three or four sync sequences. In some cases, all of the sync sequences are the same. In some cases, the sync sequences are shorter than the target sequence. In some cases, the method comprises using the sync sequences to align the target sequence datasets.

In some embodiments, the multi-pass sequence has an accuracy of Q6, Q10, Q20, Q30, Q40, or better. In some embodiments, the concatemer comprises at least at least 5 copies, optionally at least 8 copies, of the target sequence. In some embodiments, the concatemer comprises a calibration sequence. In some embodiments, the providing the concatemer comprises circularizing a nucleic acid fragment comprising the target sequence to product a circular nucleic acid; and using the circular nucleic acid as a template for rolling circle replication, thereby providing a concatemer.

In a second aspect, the present invention provides a nanopore sequencing method with single nanopore resolution calibration comprising: i) providing a non-naturally occurring nucleic acid molecule comprising a calibration sequence and a target sequence; ii) nanopore sequencing the nucleic acid molecule, thereby obtaining calibration information and target sequence information; iii) using the calibration information and the target sequence information to determine the target sequence.

In some embodiments, step iii) further comprises generating a nanopore specific base call model from the calibration information and applying the nanopore specific base call model to the target sequence information. In some cases, the method further comprises nanopore sequencing a plurality of copies of the nucleic acid molecule with a plurality of nanopores. In some cases, the method further comprises nanopore sequencing a plurality of copies of the target sequence with a single nanopore. In some cases, the method comprises providing a non-naturally occurring concatemer nucleic acid molecule containing the plurality of copies of the target sequence. In some cases, the providing the concatemer nucleic acid comprises rolling circle replication.

In a third aspect, the present invention provides a concatemer nucleic acid comprising a plurality of copies of a target sequence and a plurality of non-target sync sequences having a predetermined sequence, wherein the non-target sync sequences are positioned between adjacent copies of the target sequence, wherein the concatemer is physically associated with a nanopore. In some embodiments, the concatemer nucleic acid further comprises a calibration sequence, wherein the calibration sequence is predetermined. In some embodiments, the concatemer nucleic acid contains at least 10 copies, at least 50 copies, or at least 100 copies of the target sequence.

In a fourth aspect, the present invention provides a composition comprising a library of concatemer nucleic acids, wherein the concatemer nucleic acids of the library each comprise a plurality of copies of a target sequence and a plurality of non-target sync sequences having a predetermined sequence, wherein the non-target sync sequences are positioned between adjacent copies of the target sequence. In some embodiments, the concatemer nucleic acids each contain at least 10, at least 50, or at least 100 copies of the target sequence. In some embodiments, the library contains at least 1,000 different target sequences, optionally at least 10,000 different target sequences. In some embodiments, the target sequences comprise mammalian RNA or genomic DNA sequences. In some embodiments, the target sequences comprise human RNA or human DNA sequences.

In a fifth aspect, the present invention provides an array of nanopores, wherein each nanopore of the array is physically associated with a concatemer nucleic acid, wherein the concatemer nucleic acid comprises a plurality of copies of a target sequence and a plurality of non-target sync sequences having a predetermined sequence, and wherein the non-target sync sequences are positioned between adjacent copies of the target sequence. In some embodiments, each nanopore of the array is physically associated with a concatemer nucleic acid containing a structurally different target sequence.

In a sixth aspect, the present invention provides a massively-parallel, randomly-distributed, nanopore sequencing device comprising: a surface comprising a plurality of randomly distributed nanopores, wherein at least 10% of the randomly distributed nanopores are operably linked to a unique electrode. In some embodiments, fewer than 50% of the nanopores are operably linked to a unique electrode. In some cases, at least 100 million nanopores are operably linked to a unique electrode. In some embodiments, the device comprises an ordered array of electrodes, each electrode configured to be capable of operably linking with a nanopore.

DETAILED DESCRIPTION OF THE INVENTION

I. Overview

Current strategies for increasing accuracy of sequence information from single molecule sequencing platforms are inadequate. In contrast, the Multi-Pass Sequencing (MPS) methods disclosed herein generate accurate sequence while retaining the advantages of long read length and speed. MPS finds particular application for use with nanopore sequencing, and is also used advantageously in combination with other single molecule sequencing methods such as nanochannel-based sequencing (e.g., Schmidt, 2004, "A nanoelectrode lined nanochannel for single molecule sequencing" (Thesis) Carnegie Mellon University) or zero-mode waveguide sequencing (e.g., SMRT Pacific Biosciences). Thus, although the discussion below is focused on the application of MPS to nanopore sequencing, it will be appreciated that the same concatemeric molecules, libraries, and analytical methods can be used in any suitable SMS method.

As used herein, "nanopore sequencing" involves the use of a transmembrane nanopore to determine the sequence of a polynucleotide. Typically, nanopore sequencing involves the translation (or, equivalently, "translocation") of a polynucleotide through the transmembrane nanopore. As the polynucleotide is translated through the nanopore, one or more electrical properties at the nanopore change in a sequence-dependent manner. By detecting such changes in one or more electrical properties (e.g., ionic current through the nanopore), the base sequence of the polynucleotide can be deduced. Exemplary nanopores include, without limitation, biological nanopores (alpha hemolysin, *Mycobacterium smegmatis* porin A) and solid state nanopores. Translocation of the polynucleotide through the nanopore can be mediated by an applied voltage, an enzyme (e.g., a polymerase), or a combination thereof.

In some cases, however, nanopore sequencing can be performed without a translation of the polynucleotide through the nanopore. For example, a nanopore can be used to detect polymerization or hybridization products of a polynucleotide. In an exemplary embodiment, a polynucleotide can be physically associated (e.g., directly or indirectly covalently linked) to a membrane embedded nanpore and a polymerase in the presence of base-specific labeled nucleotides. The polymerase can perform template directed polymerization with the polynucleotide as the template molecule. In some cases, the base-specific labeled nucleotides are different sizes for each different base. As the labeled nucleotides are incorporated into a newly synthesized strand, the labels can be released from the nucleotide by the polymerase. The released labels can translate through the nanopore (e.g., as mediated by an applied voltage potential across the nanopore), where they alter one or more electrical properties of the nanopore (e.g., ionic current through the nanopore) in a sequence specific manner. By detecting such changes in one or more electrical properties, the base sequence of the polynucleotide can be deduced.

In an exemplary embodiment, the base-specific labeled nucleotides contain different length polymer linkers, thus providing a sequence dependent signal upon translocation through a nanopore. A variety of polymer linkers are known in the art, such as polyethylene glycol linkers, or derivatives thereof. In some cases, the linkers are conjugated to the nucletide and an additional identifiable moiety. In some cases, the additional identifiable moiety is selected to enhance the generation of a sequence-specific signal. An exemplary additional identifiable moiety is a coumarin molecule, a coumarin based dye, or a derivative thereof. See, e.g., Kumar et al. Scientific Reports, 2:684 pp. 1-8 (2012); U.S. Pat. No. 8,088,575; U.S. Patent Appl. Publication No. 2013/0264,207; and International Patent Publication Nos. WO 2007/146,158; and WO 2013/191,793, the contents of which are hereby incorporated by reference in their entirety.

In the multi-pass sequencing methods of the invention, the sequence of a single polynucleotide comprising multiple copies of a target sequence is determined by single molecule sequencing (e.g., nanopore sequencing). Thus, in some embodiments, the same target sequence is sequenced multiple times as a single concatemer polynucleotide, or a portion thereof, passes through the nanopore. In some embodiments, the same target sequence is sequenced multiple times by contacting a concatemer polynucleotide template with a polymerase in the presence of base-specific labeled nucleotides. The polymerase can perform template directed polymerization to generate a polymerization product that is complementary to the concatemer template. The base-specific nucleotide labels can be released from the nucleotides by the polymerase as the nucleotides are incorporated into the polymerization product. The released base-specific labels can then pass through the nanopore.

A "multiple pass sequence data set" is thus obtained for the polynucleotide, and a "sequence data set" is determined for each copy of the target sequence (i.e., a plurality of sequence data sets are obtained). A highly accurate (or "HighQ") target sequence is determined based on the plurality of sequence data sets. This approach, in combination with other innovations described below, allows improved base-call accuracy and sequencing efficiency. Among other advantages, MPS avoids or reduces the effects of variation resulting from making measurements from different nanopores, which may be located at different locations in an array, at different times, with different polynucleotide molecules. Each of these parameters and others are sources of noise using conventional methods. For example, individual nanopores can vary greatly in their electrical properties and in their electrical response to translation of a nucleotide base through the pore, nanopores in different locations on an array may be influenced by temperature gradients or other environmental differences, and changes over time due to temperature, voltage, current, or power fluctuations can affect the electrical properties of a nanopore with consequential changes in the signal.

In some embodiments of the invention, copies (or "iterations" or "repeats") of target sequence are separated by predetermined "synchronization sequences" (generally referred to as "sync sequences"). Sync sequences are known (i.e., pre-determined), generally short, non-target sequences that demarcate the boundaries (beginning and/or end) of target sequence repeats. The sync sequences can detected and used to combine multiple target sequence repeats from a concatemer. In one approach, the sync sequences are used to determine a unified time duration for a target sequence (e.g., an average of the target sequence translocation time for repeats of the same concatemer) and the target sequence datasets (information generated by sequencing the target sequences) are standardized based on the unified time duration and combined to produce a HighQ target sequence.

In some embodiments of the invention, the concatemer comprises one or more copies of a calibration sequence. The signal produced by translocation or polymerization of the calibration sequence (i.e., the "calibration data set" or "calibration information") can be used to model base-calling for each channel and, for example, to equalize signals or data sets generated at different nanopores or from the same nanopore at different times.

The MPS methods of the invention may be used to determine a large number of HighQ target sequences from a source nucleic acid. The HighQ target sequences may then be assembled using art-known methods to produce longer sequences.

II. Properties and Production of Concatemers

The present invention provides methods for improved nanopore sequencing of a target sequence by (i) making a nucleic acid concatemer containing multiple copies of the target sequence, (ii) translocating the concatemer (or a portion of the concatemer containing at least three copies of the target sequence) through a nanopore, while measuring an electrical property that changes in a sequence dependent manner as the concatemer translocates through the nanopore, and using the measurements obtained in step (ii) to determine a sequence of the target.

In some cases, the present invention provides methods for improved nanopore sequencing of a target sequence by (i) making a nucleic acid concatemer template containing multiple copies of the target sequence, and (ii) contacting the concatemer template (or a portion of the concatemer containing at least three copies of the target sequence) with a polymerase to perform template directed polymerization in the presence of base-specific labeled nucleotides. Incorporation of the labeled nucleotides into a polymerization product can then release or cleave the base-specific nucleotide labels, which labels can then be translated through a nanopore. An electrical property that changes in a sequence dependent manner as the base-specific labels translocate through the nanopore can be measured and used to determine a sequence of the target.

As used herein, "concatemer" refers to a nucleic acid comprising multiple copies of a monomeric sequence ("monomers") linked in tandem. For concatemers of the present invention, the monomer comprises the target sequence and, optionally, comprises one or more sync sequences. In some embodiments, the monomer comprises both one or more sync sequences and one or more distinct calibration sequences. The concatemer may also include other sequences that are not contained in the monomers, including one or more calibration sequences, adaptor sequences flanking a plurality of linked monomers, and the like. It will be appreciated that the term "monomer" is used to refer to a structure (relationship of sequence elements) and is not intended to require or imply a particular method of construction of the concatemer.

The concatemer nucleic acid is typically DNA, but can be any sequenceable nucleic acid including DNA, RNA, or a chimeric nucleic acid. In some embodiments the concatemer is a single stranded nucleic acid, such as a single-stranded DNA. The concatemer may be at least about 1 kb in length and usually is longer, e.g., at least about 2, 3, 4, 5, 7, 10, 12, 14, 16, 18, 20, 25, 30, 35, 40, or 50 kb or longer. In some embodiments, the concatemer is at least about 50, 60, 70, 80, 90, 100, 150, 200, 250, or 300 kb or longer. In some embodiments the concatemer is from 1 kb to about 300 kb in length, sometimes from about 10 kb to about 200 kb in length. In some embodiments the concatemer is 8 kb to 20 kb.

The number of copies of a target sequence in a concatemer will depend on the length of the target sequence, the length of the concatemer, and the lengths of non-target sequences such as sync sequences and calibration sequences in the concatemer. In some embodiments, the concatemer contains at least 2, at least 3, at least 4, at least 5, at least 6, at least 7, at least 8, at least 9, at least 10, at least 11, at least 12, at least 15, at least 20, at least 50, or at least 100 copies of a target sequence. In some embodiments, the concatemer contains 5-300 copies of a target sequence. In some embodiments, the concatemer contains 5-12 copies of a target sequence.

In some embodiments, the concatemer contains 5-12 copies of a target sequence and the target sequence is 1-2 kb in length.

In some embodiments, the size of the target sequence is at least about 250 nucleotide bases in length. In some embodiments, the target sequence is at least 300, 350, 400, 450, 500, 550, 600, 650, 700, 750, 800, 850, 900, or 950 nucleotide bases in length. In some cases, the target sequence is at least 1, 2, 3, 4, 5, 6, 7, 8, 9, or 10 kb in length. In some embodiments, the target sequence is from 100, 200, 300, 350, 400, 450, 500, 550, 600, 650, 700, 750, 800, 850, 900, or 950 nucleotide bases in length to 1, 2, 3, 4, 5, 6, 7, 8, 9, or 10 kb in length. In some embodiments, the target sequence is from 100 nucleotides to 10 kb in length, from 200 nucleotides to 10 kb in length, from 300 nucleotides to 10 kb in length, from 400 nucleotides to 10 kb in length, from 500 nucleotides to 10 kb in length, from 100 nucleotides to 5 kb in length, from 200 nucleotides to 5 kb in length, from 300 nucleotides to 5 kb in length, from 400 nucleotides to 5 kb in length, from 500 nucleotides to 5 kb in length, from 100 nucleotides to 2 kb in length, from 200 nucleotides to 2 kb in length, from 300 nucleotides to 2 kb in length, from 400 nucleotides to 2 kb in length, from 500 nucleotides to 2 kb in length, from 100 nucleotides to 1 kb in length, from 200 nucleotides to 1 kb in length, from 300 nucleotides to 1 kb in length, from 400 nucleotides to 1 kb in length, or from 500 nucleotides to 1 kb in length.

In embodiments in which the monomers comprise target and one or more sync sequences, the size of the monomer sequence may be at least about 260 nucleotide bases in length in some embodiments. In some embodiments, the monomer sequence comprising target and one or more sync sequences is at least 300, 350, 400, 450, 500, 550, 600, 650, 700, 750, 800, 850, 900, or 950 nucleotide bases in length. In some cases, the monomer sequence is at least 1, 2, 3, 4, 5, 6, 7, 8, 9, 10, 12, 14, 16, 18, 20, or 25 kb in length. In some embodiments, the monomer sequence comprising target and one or more sync sequences is from 300, 350, 400, 450, 500, 550, 600, 650, 700, 750, 800, 850, 900, or 950 nucleotide bases in length to 1, 2, 3, 4, 5, 6, 7, 8, 9, or 10 kb in length. In some embodiments, the monomer sequence comprising target and one or more sync sequences is from 100 nucleotides to 10 kb in length, from 200 nucleotides to 10 kb in length, from 300 nucleotides to 10 kb in length, from 400 nucleotides to 10 kb in length, from 500 nucleotides to 10 kb in length, from 100 nucleotides to 5 kb in length, from 200 nucleotides to 5 kb in length, from 300 nucleotides to 5 kb in length, from 400 nucleotides to 5 kb in length, from 500 nucleotides to 5 kb in length, from 100 nucleotides to 2 kb in length, from 200 nucleotides to 2 kb in length, from 300 nucleotides to 2 kb in length, from 400 nucleotides to 2 kb in length, from 500 nucleotides to 2 kb in length, from 100 nucleotides to 1 kb in length, from 200 nucleotides to 1 kb in length, from 300 nucleotides to 1 kb in length, from 400 nucleotides to 1 kb in length, or from 500 nucleotides to 1 kb in length.

In some cases, the number of copies of target sequence in the concatemer is less than, or is about equal to, the length of the concatemer divided by the number of target sequence copies and the length of the target sequence. In some cases, the concatemer comprises a number of copies of template sequence that is less than, or is about equal to, the length of the concatemer divided by the length of a monomer comprising the target sequence and one or two sync sequences. Generally, a concatemer of a given length can contain a larger number of template copies than a shorter concatemer.

As described herein, the concatemer nucleic acid generally contains at least three copies of the target sequence. Thus, the length of the target sequence can generally be any sequence length up to approximately one-third the length of the concatemer nucleic acid.

It is estimated that, in some embodiments, the multi-pass sequencing methods described herein can provide sequence reads with an accuracy of at least about Q30 when combining sequence information that contains less than about 8-fold redundancy. Thus, the multi-pass sequencing methods can provide Q30 reads of a 1 kb target sequence using a concatemer of less than about 8-10 kb. Moreover, since the multi-pass sequencing methods provided herein can generate concatemer nucleic acids that are much longer than 10 kb, and the single molecule sequencing methods can, in some cases, provide sequence reads that are much longer than 10 kb, even higher levels of accuracy can be obtained.

For example, sequence read lengths of up to 100 kb have been reported. Therefore, Q30 sequence accuracy can be provided by contacting a nanopore with a concatemer of approximately 100 kb or longer containing 8-10 copies of a 10 kb template sequence. Alternatively, even higher levels of accuracy such as Q40 can be provided by utilizing a shorter template or a longer concatemer, or a combination thereof. Additional permutations of concatemer length, template sequence length, and desired sequence accuracy will be apparent to one of skill in the art.

In some embodiments, the concatemer contains target or monomer copies linked in the same 5' to 3' orientation. In some embodiments, the concatemer contains a plurality of template sequence copies linked in a head-to-tail configuration, a random orientation or an unpredictable orientation. It will be understood that the orientation(s) of template and monomer sequences may be tied to the method used to produce the concatemer.

As discussed below in Section V, usually heterogeneous libraries or populations of polynucleotides (such as a plurality of different genomic fragments) are sequenced. In some libraries or populations, the source nucleic acids may be heterogeneous in size (e.g., an mRNA population). In these cases, the resulting population of concatemers may contain a range of target sizes.

In one embodiment, the concatemers of the library contains at least $10^4$, sometimes at least $10^5$, sometimes at least $10^6$ different target sequences. In one embodiment the concatemers of the library contain or contain at least, on average, 4-15 or 5-10 copies of a target sequence and the median or average length of the target sequences is in the range of 1-2 kb in length.

Exemplary target sequences may be, for example and without limitation, genomic DNA, complementary DNA transcribed from mRNA or rRNA, or RNA (e.g., mRNA, rRNA, and the like), from an animal (e.g., humans, mammal or vertebrate), plant, bacteria, fungi or virus, for example. In some embodiments a reference sequence is available for a nucleic acid source (e.g., human genomic DNA).

III. Synchronization (Sync) Sequences

In some embodiments, the non-naturally occurring concatemer nucleic acid contains a plurality of copies of the target sequence and one or more non-target sync elements. The sync elements are predetermined non-target sequences positioned between adjacent copies of the target sequence. Typically the concatemer comprises monomeric units comprising a target sequence linked at one or both ends to a sync sequence. Typically, the sync sequences are shorter than the target sequence. In some embodiments, exemplary non-target sync sequences are 6-25 bases in length.

In some embodiments, the sync sequences are designed to provide a signal that is readily distinguishable from the target sequence and/or provides a signal with particular characteristics in the sequencing platform. Sync sequences can be used generate specific electrical signal patterns that facilitate recognition, capture, or detection. For example, the sync sequences may have a sequence that, in the sequencing platform used, gives a clear unambiguous signal.

In some cases, the sync sequences comprise multiple short tandem repeat sequences. For example, the sync sequence can comprise multiple copies of one or more dinucleotide repeat sequences. As another example, the sync sequence can contain multiple copies of one or more trinucleotide repeat sequences. One of skill in the art will appreciate that the monomer repeat length can be any one of 1, 2, 3, 4, 5, 6, 7, 8, 9, or 10 nucleotides or more. Moreover, a sync sequence can contain combinations of monomer repeats. For example, the sync sequence can contain one or more copies of two or more different dinucleotide repeats. As another example, the sync sequence can contain one or more copies of a dinucleotide repeat and one or more copies of a trinucleotide repeat. In some cases, the sync sequence contains alternating copies of at least two different repeat monomers.

Exemplary sync sequences can include but are not limited one or more of the following sequences: SEQ ID NO:1 (AGAGAGAGAGAGAGAGAGAG); SEQ ID NO:2 (ATGATGATGATG); or SEQ ID NO:3 (CAGCAGCAG).

In some embodiments, the sync sequence is 4, 5, 6, 7, 8, 9, 10, 11, 12, 13, 14, 15, 16, 17, 18, 19, 20, 21, 22, 23, 24, 25, 26, 27, 28, 29, or 30 nucleotides in length. In some cases, the sync sequence is 4-25, 6-25, or 10-25 nucleotides in length. In some embodiments, the sync sequence is 10-15 or 15-20 nucleotides in length. In some cases, the sync sequence is at least about 6, 7, 8, 9, 10, 11, 12, 13, 14, or 15 nucleotides in length. In some cases, the sync sequence is less than about 35, 34, 33, 32, 31, 30, 28, 27, 26, 25, 24, 23, 22, or 21 nucleotides in length.

In some embodiments, the sync sequences may be used for calibration as well as for demarcation of the target sequence boundaries. Although they may be used for calibration, sync sequences differ from "calibration sequences," discussed below, based at least on position. As used herein, sync sequences are represented in all or nearly all of the repeated monomers and, for example, there may be about as many copies of sync sequences as there are copies of calibration sequences. In contrast, "calibration sequences," are not represented in the monomer, and there may be as few as one copy per concatemer of a calibration sequence. In some embodiments, there is no more than one, no more than 2, no more than 3 or no more than 5 calibration sequences per concatemer. In some embodiments both sync sequences and calibration sequences are present, and the individual sync sequences are significantly shorter than the calibration sequences (e.g., one-half or one-quarter the length).

For example, for illustration and not limitation, the concatemer may include any of the following structures (T=target sequence, S=sync sequence, $S^1$ and $S^2$ are different sync sequences, C=calibration sequence, N=3-300):
  i) $[S-T]_N$
  ii) $C-[S-T]_N$
  iii) $C-[S-T]_N-C$
  iv) $C-[S-T]_N-C-[S-T]_N-C$
  v) $C-[S^1-T-S^2]_N$
and the like.

In some embodiments, a monomer (and concatemer) may include two or more different target sequences (e.g., $T^1$ and $T^2$). An exemplary structure would be:
  vi) $[S-T^1-S-T^2]_N$ The use of sync sequences in data analysis is discussed below in Section VI.

IV. Calibration Sequences

In some embodiments, the concatemer contains at least one calibration sequence. In some embodiments the concatemer comprises two or more calibration sequences, which may be the same or different. Calibration sequences are used to optimize a base-call model, to allow variations in the properties of individual nanopores to be identified and the signal normalized (e.g., normalize datasets), to detect or reject outliers, and/or to provide a quality or predicted base-call accuracy score for one or more datasets. The calibration sequence can be any position with the nucleic acid. In some cases, the calibration sequence is at a known position in the nucleic acid (e.g., at the 5' end, the 3' end, or at the 5' and 3' end of the nucleic acid).

As noted above, in some cases, a sync sequence can be used for the same purposes as a calibration sequence (e.g., used to optimize a base-call model, etc.). However, the optimal nucleotide composition for a calibration sequence may not be the composition for a sync sequence intended for demarcation of target sequence boundaries. As noted above, calibration sequences are generally longer than sync sequences.

In some cases, a concatemer nucleic acid molecule contains a single calibration sequence and multiple sync sequences. In some cases, a concatemer nucleic acid molecule contains multiple calibration sequences and multiple sync sequences.

Calibration sequences can be used to combine sequence information from multiple nanopores, or optimize the read accuracy for each sequence read. For example, a plurality of copies of a template sequence, wherein each copy contains a calibration sequence, can be contacted with a plurality of nanopores. The sequence information can be obtained and the calibration sequences identified. The calibration sequences can then be used to normalize the sequence information from each nanopore so that it can be combined (e.g., averaged). As another example, the calibration sequences can be used to refine a general base call model for each nanopore, or for each sequence read.

V. Generating DNA Concatemers and Concatemer Libraries

Concatemers for use according to the present invention can be generated by a variety of methods known in the art. For example, the concatemer can be generated by ligation, rolling circle replication (also called rolling circle amplification), or a combination thereof. In general, sequencing is carried out using a heterogeneous library of DNA concatemers, where the concatemers comprise a variety of different target sequences (which may be derived from a the same or different source nucleic acid). For example, if the source nucleic acid is genomic DNA of an organism, members of the library may comprise sequences corresponding to different genomic DNA fragments. If the source nucleic acid is mRNA, members of the library may comprise cDNA sequences corresponding to individual mRNA molecules. If the source nucleic acid is a microbiome, members of the library may comprise nucleic acid sequences from individual microorganisms. In some embodiments concatemers within a given library are approximately uniform in size. In some embodiments, especially when targets from different source nucleic acid (e.g., different subjects) are comingled, the concatemer may comprise barcodes or unique molecular identifiers (UMIs) to identify the source or molecule. Optionally the barcode may be in the monomer. In some embodiments, individual populations of target sequences are constructed using different sync sequences, so they can be identified when comingled.

In some cases, the concatemer is generated by ligation. For example, multiple copies of a target polynucleotide sequence can be ligated in a reaction vessel under conditions that promote intermolecular ligation, thus producing concatemers of the polynucleotide containing multiple copies of the target sequence. See, e.g., Szostak, 1992, *Biochemistry* 31, 10643-51.

In some cases, the concatemer is generated by rolling circle replication (RCR, also called also called rolling circle amplification). In this case, a linear molecule containing one or more monomer sequences (e.g., a target sequence and optionally sync sequence(s)) can be prepared by any number of well-known methods, including ligation of a sync sequence to a target sequence, tagmentation, etc., and circularized for RCR. Alternatively, a sync sequence (for example) can be inserted into an existing circular polynucleotide.

In some cases, a linear molecule comprising one or more monomers is circularized for rolling circle replication by ligation of an adaptor to the 5' end of a nucleic acid fragment and a second adaptor to the 3' end of the nucleic acid fragment and amplifying the fragment. The adaptors can be configured to contain complementary single-strand ends that hybridize to each other to form a circularized nucleic acid fragment.

RCR methods are well known. Generally a circular polynucleotide is contacted with a polymerase, and optionally a helicase or single-strand nucleic acid binding protein. As replication of the circular template occurs, the newly synthesized nucleic acid strand displaces the strand synthesized in the previous revolution giving a polymerization product containing a linear series of sequences (monomers) complementary to the circular template strand. The circular template can be double stranded or single stranded. Guidance for selecting conditions and reagents for RCR reactions is available in many references available to those of ordinary skill, as evidence by the following that are each incorporated by reference: Gilbert & Dressier, 1968, *Cold Spring Harbor Symposium. Quant. Biol.* 33:473-84; Baker & Kornberg, 1992, *DNA Replication* (Freeman, N.Y.); and U.S. Pat. Nos. 5,648,245; 5,714,320; 6,143,495; 5,426,180; 5,854,033; 6,143,495 and 5,871,921. Additional methods for generating a circularized template or performing rolling circle amplification to generate a concatemer nucleic acid include those disclosed in U.S. Pat. No. 8,445,196.

Generally, RCR reaction components comprise single-stranded DNA circles, one or more primers that anneal to DNA circles, a DNA polymerase having strand displacement activity to extend the 3' ends of primers annealed to DNA circles, nucleoside triphosphates, and a conventional polymerase reaction buffer. Such components are combined under conditions that permit primers to anneal to DNA circles and be extended by the DNA polymerase to form concatemers of DNA circle complements. An exemplary RCR reaction protocol is as follows: In a 50 µL reaction mixture, the following ingredients are assembled: 2-50 pmol circular DNA, 0.5 units/µL phage phi29 DNA polymerase, 0.2 µg/µL BSA, 3 mM dNTP, 1×phi29 DNA polymerase reaction buffer (Amersham). The RCR reaction can be carried out at 30° C. for 12 hours. In some embodiments, the concentration of circular DNA in the polymerase reaction may be selected to be low (approximately 10-100 billion circles per ml, or 10-100 circles per picoliter) to avoid entanglement and other intermolecular interactions.

The concatemer or concatemer library may be stored prior to sequencing, and may be sequenced in the same fashion as conventional non-concatemerized polynucleotides.

VI. Data Analysis

As described herein, a concatemer nucleic acid containing a plurality of target sequences, optionally sync sequences, and optionally calibration sequence(s) can be translocated though a nanopore while measuring an electrical property that changes in a sequence dependent manner. As also described herein, a concatemer nucleic acid containing a plurality of target sequences, optionally sync sequences, and optionally calibration sequence(s) can be contacted with a polymerase in the presence of base-specific labeled nucleotides. The polymerase can perform template directed polymerization to generate a polymerization product that is complementary to the concatemer template. The base-specific nucleotide labels can be released from the nucleotides by the polymerase as the nucleotides are incorporated into the polymerization product. The released base-specific labels can then pass through the nanopore while an electrical property that changes in a label specific manner is detected.

The measured electrical properties can include, but are not limited to, one or more electrical properties selected from the group consisting of current, change in current, voltage, change in voltage, resistance, change in resistance, inductance, change in inductance, capacitance, change in capacitance, reactance, and change in reactance. Generally, a nanopore is located in a membrane immersed in, or separating two compartments. Typically a nanopore is embedded in a membrane with high electrical resistance, an ionic current is passed through the nanopore by setting a voltage potential across the membrane, and changes in current are measured as a polynucleotide or base-specific labels translocate through the nanopore from one compartment to the other.

The sequence information can be represented by a continuous set of electrical signals as a polynucleotide or base specific labels are translated through a nanopore. Alternatively, the sequence information can be represented by a sample of measured electrical signals as a polynucleotide or base-specific labels are translated through a nanopore. For example, a nucleotide-specific or label-specific electrical property of a nanopore can be monitored at a frequency (e.g., 10-100 kHz) sufficient to detect a sequence information and deduce the sequence of a polynucleotide. A sufficient sampling frequency can vary based on the speed and manner at which a polynucleotide or base specific labels are translated. In general, the sampling frequency should be sufficient to detect at least one data point of the sequence information for each translated nucleotide base, k-mer, or label. Detection of multiple data points per translated nucleotide base, k-mer, or label is generally desirable. The sequence information set can be represented and stored in a graphic, analog or digital format, and is referred to here as a sequence dataset.

A sequence dataset is used to determine the sequence of a polynucleotide by correlating measured electrical property values, or changes in the measured electrical property values (typically changes in current) with expected (e.g., empirically determined) values for translocation of different nucleotide bases, combinations of bases, or base-specific labels. In some cases, the sequence is determined by correlating a set of measured electrical property values, or changes in such values, for a set of k-mer nucleotides with expected values for translocation of the k-mer. Application of k-mer measurement and analysis algorithms for nanopore sequencing are known in the art and described in, e.g., International Patent Publication WO 2014/096830. Typical values of k include, 2, 3, 4, 5, 6, 7, 8, 9, or 10. In some embodiments, k-mers are detected and analyzed using a hidden markov model. For example, a Viterbi algorithm can be utilized to assign sequences to detected k-mer nucleotides. See, e.g., Timp et al, 2012, *Biophys J.* 102:L37-9.

Conventional nanopore sequencing generates a dataset corresponding to one copy of a target sequence. MPS generates a "multi-pass sequence dataset" (a set of discrete or continuous measurements of the electrical properties of a nanopore as a concatemer polynucleotide is translated through the nanopore) corresponding to a plurality of monomers comprising a plurality of target sequences (e.g., a plurality of copies of the target sequence and associated sync sequence) and calibration sequences. Target sequence is determined using the multi-pass sequence dataset by (1) extracting the data corresponding individual copies of the target sequence ("target sequence data sets"); and (2) combining the target sequence data sets to generate the high-accuracy target sequence ("HighQ target sequence"). In one approach, each target sequence data set is converted to a nucleotide sequence, and the plurality of nucleotide sequences are used to generate a consensus (HighQ) target sequence. In another approach, a plurality of target sequence data sets are combined to generate a 'consensus' data set, and a HighQ target sequence is derived from the 'consensus' data set.

Data corresponding to individual copies of the target sequence can be extracted by identifying repeated patterns in the multi-pass sequence dataset, corresponding to multiple tandem copies of the target sequence. When the concatemer includes sync sequences the sync sequences may be used to precisely demarcate signal boundaries corresponding to target sequence boundaries. Portions of the multi-pass sequence dataset that do not correspond to the known sync sequences can be identified as target sequences.

In one approach, the sync sequences are used to define a time duration (time of polynucleotide transit through the nanopore) for each target sequence. A unified time duration (e.g., a statistical average or median nanopore translation time or polymerization time of a plurality of copies of a target sequence) is determined and each of the target sequence signals (or datasets) is aligned or standardized to match the unified time duration. The datasets can then be combined (e.g., averaged) to reduce noise levels. A base-calling model can then be applied to the resulting combined dataset to obtain the target sequence with high accuracy. In some cases, the base-calling model is a general base calling model. In some cases, the base calling model is optimized to one or more characteristics of the combined dataset, e.g., by optimizing the base calling model against portions of the dataset corresponding to one or more calibration sequences.

The target sequence data sets (corresponding individual copies of target sequence) can be combined (e.g., averaged) and used to determine a target sequence. Methods for combining multiple datasets include, but are not limited to, determining an average (mean or median) dataset from the plurality of single-pass datasets. The averaging can be performed, e.g., at a signal event level (e.g., each signal event is averaged), a feature level (e.g., datasets are analyzed to identify features, and features are averaged together), or a k-mer level (e.g., features corresponding to k-mers can be averaged). Such averaging methods can be particularly useful, where the primary source of error or noise is random. In such cases, the random errors can partially or completely cancel out when a sufficient number of datasets are included in the combining step.

In some cases, multiple target sequence datasets extracted from a multi-pass dataset are combined by determining a weighted average dataset from the plurality of target sequence datasets. The weighted average can be determined by calculating and applying a weight for each dataset, for each detected electrical event, for each identified feature, or for each region of a dataset corresponding to translocation of a single base, a group of bases (e.g., corresponding to a feature, or a k-mer), or a base-specific label. In some case, the weight is calculated based on a portion of the dataset and applied to a larger portion of the dataset, or the entire dataset. For example, the weight can be calculated based on the portion of the dataset corresponding to one or more calibration sequences or one or more sync sequences. In some cases, the weight is calculated as a measure of expected probability of base call accuracy.

The weight can be calculated from local or global properties of the dataset, such as amplitude (e.g., average peak amplitude, maximum peak amplitude, etc.), peak shape, resolution, peak overlap, etc. In some cases, the weight is calculated based on the presence, absence, or degree of one or more of the following indicators of low-accuracy regions: a very short duration electrical signal (e.g., change in current); an unusually long duration electrical signal (e.g., change in current); an electrical signal having an amplitude that is between the average amplitude distributions observed for two different bases, k-mers, or base-specific labels (indicating a high probability of an erroneous base call); a large duration between adjacent electrical signals (e.g., between changes in current); or a high level of noise at a given dataset region (e.g., due to baseline drift, random or systematic cross-talk between proximal nanopores, or sequence dependent effects).

In some cases, datasets (e.g., target sequence datasets extracted from a multi-pass dataset) can be filtered before, or after, combining. In some cases, the filtering step can be used to remove outlier datasets and improve the accuracy of a resulting combined dataset. In some cases, datasets, e.g., multi-pass, target sequence, or combined datasets, can be subject to a low-pass, band-pass, or high-pass filter to remove systematic noise. As another example, individual datasets can be analyzed to determine a measure of noise, and rejected when the value of the measured noise is above a set threshold or a dynamically determined threshold. Various methods for filtering datasets are known in the art and include, e.g., Fourier transform based methods. Various methods for determining the level of noise of an dataset, or portion thereof, or filtering out noisy datasets, or portions thereof, are known in the art and include those described in, e.g., U.S. Patent Application Publication No. 2014/0248, 608, herein incorporated by reference in the entirety.

In some cases, datasets (e.g., target sequence datasets extracted from a multi-pass datasets) can be normalized before combining. Normalization algorithms can be used to ensure that electrical signal events from multiple datasets are comparable. In some cases, normalization places the datasets on an absolute scale. In other cases, normalization places the datasets on a relative scale. Normalization algorithms can include scaling algorithms. For example, a scaling algorithm can be applied to a plurality of datasets to ensure that maximum or minimum electrical signals are scaled to correspond across different datasets. Additional filtering, normalization, or scaling methods are described in, e.g., in U.S. Pat. No. 8,652,779; and U.S. Patent Application Publication Nos. 2010/0331194; and 2014/0248608, herein incorporated by reference in the entirety.

In some embodiments, a base sequence is determined for each target sequence dataset, e.g., from a multi-pass dataset, and a consensus sequence is determined based on the plurality of base sequences using well-known methods. Methods for aligning and generating consensus sequences are well-known in the art. For example, the program PILEUP from the Wisconsin Package GCG nucleic acid analysis software suite can be utilized. See, e.g., Curr. Protoc. Bioinformatics 2003 February; Chapter 3: Unit 3.6. As another example, a consensus sequence may be generated by selecting the most frequently assigned base for each nucleotide position in the aligned set of base sequences.

In some cases, the called bases of individual target sequences can be given a weight, e.g., a quality or predicted base-call accuracy score. In some cases, the weight is provided for each called base. In some cases, the weight is provided for a group of called bases (e.g., groups of 2, 3, 4, 5, 6, 7, 8, 9, 10 or more continuous bases). A weight can be calculated from local or global properties of a sequence dataset (e.g., target sequence, multi-pass, or combined datasets), such as amplitude, peak shape, resolution, peak overlap, etc. In some cases, a weight is calculated based on the presence, absence, or degree of one or more of indicators of low-accuracy regions, as described above.

The weight can be used to generate a consensus sequence. For example, a consensus sequence may be generated by: selecting the most frequently assigned base for each nucleotide position in the aligned set of base sequences; selecting the highest weighted assigned base for each nucleotide position in the aligned set of base sequences; or, a combination thereof. For instance, where the number of different assigned bases at a position is equal to or greater than the number of aligned base sequences, the weight can be used to break the tie or overcome the ambiguity.

Base calling of a target sequence dataset or a combined dataset can be performed with a generalized or a nanopore specific base call model. In some cases, the generalized based call model is provided by a commercial supplier of the nanopore device. For example, dataset from a MinION device can be uploaded to the cloud-based Mitrichor service that analyzes the data to determine the corresponding nucleotide sequence and provides a file containing the nucleotide sequence along with other information.

As discussed above, in some embodiments, a nanopore specific base call model can be generated by detecting portions of a dataset corresponding to known sequences or features in a nucleic acid (e.g., corresponding to a calibration sequence of a concatemer) and optimizing the base call model to the particular electrical and physical properties of the nanopore from which the dataset is derived. For example, a nucleic acid fragment can be labeled with a known sequence or a non-nucleic acid moiety that can provide an identifiable signal as the nucleic acid is translocated through the nanopore. The identifiable signal can then be utilized to calibrate the base call model for that nanopore.

Because the sync sequences are known, they can also be used to calibrate the signal. In this context, "calibrate" means refining the model of the relationship between the signal detected at the nanopore and the base sequence. The signal may vary or drift with changes in temperature, ionic environment, power fluctuations, etc. even within the timeframe of polynucleotide translation or polymerization, so that the ability to frequently calibrate against a known sync sequence (or sequences) is advantageous

VII. Signal Amplification with Base- or Sequence-Specific Labels

In some embodiments, a nucleic acid fragment containing a target sequence (e.g., a concatemer containing multiple copies of the target sequence) is labeled with one or more base-specific labels to amplify the electrical signal generated as the template sequence is translated through the nanopore. For example, the label can bind to and thereby increase the size of one or more nucleotide bases. As another example, the label can impart a charge to one or more nucleotide bases. In some cases, the label is a bidentate platinum ligand that specifically recognizes adjacent guanine residues in a target sequence. See, e.g., Teletchéa et al., 2006, *Chemistry* 12:3741-53 In some cases, the one or more base-specific labels can hydrogen bond, in a base-specific manner, to one or more nucleotide bases of the target sequence. See, e.g., U.S. Pat. No. 5,470,707.

In one embodiment, one or more hydrogen bond labels can contain a nucleoside and a variable number of phosphate groups. For example, the one or more labels can include a thymidine (e.g., deoxythymidine) with zero, one, two, or three 5' phosphates. The thymidine can hydrogen bond, in a base specific manner, to a corresponding adenosine in the target sequence. As another example, the one or more labels can include a cytidine (e.g., deoxycytidine) with zero, one, two, or three 5' phosphates. The cytidine can hydrogen bond, in a base specific manner, to a corresponding guanosine in the target sequence. As another example, the one or more labels can include a guanosine (e.g., deoxyguanosine) with zero, one, two, or three 5' phosphates. The guanosine can hydrogen bond, in a base specific manner, to a corresponding cytosine in the target sequence. The use of a variable number of phosphate groups can further amplify signal. For example, one base-specific label can contain a single 5' phosphate, while another contains two 5' phosphates, and a third contains three 5' phosphates.

US Pat. Pub. 20110236984 "DNA Sequencing Methods And Detectors And Systems For Carrying Out The Same" describes the use of coded oligonucleotides that can be hybridized to a target DNA molecule and used to detect the presence of various sequences along the target molecule.

In some embodiments, the labels are specific for one or more sync sequences. For example, the sync sequences can be labeled with a sequence specific polynucleotide hybridization probe prior to translation through the nanopore. The sequence information corresponding to the labeled sync sequences can then be detected and utilized to facilitate alignment of single-pass sequence datasets generated during multi-pass sequencing of a concatemer or during single-pass sequencing through a plurality of nanopores.

VIII. Other Sequencing Platforms

The use of concatemers, sync sequences, and calibration sequences, as described herein, can be used with other single-molecule sequencing methods. In particular, the SMRT system from Pacific Biosciences can be contacted with a concatemer to generate multi-pass sequence information. The SMRT system is a method of Single Molecule Real Time sequencing in which a single DNA polymerase is affixed to the bottom of a container that is operably linked to a zero-mode waveguide (ZMW). The ZMW creates an observation volume sufficiently confined to limit observations to a single nucleotide of DNA as it is incorporated by the polymerase. The nucleotides are labeled with a fluorophore that is cleaved off by the polymerase during the polymerization and generally diffuses out of the observation volume before the next nucleotide is incorporated. The SMRT system generally provides average read-lengths of approximately 3-9 kb, depending on sample preparation, dye chemistry, and polymerase. Thus, for example, a concatemer of approximately 9 kb can provide 9-fold redundancy for a 1 kb target sequence, using the SMRT system.

A concatemer for analysis with the SMRT system can contain additional sync or calibration sequences as desired. The multi-pass sequence information can then be combined using methods known in the art, such as those described herein, to increase the accuracy of the resulting sequence. For example, sequence datasets can be combined by averaging or weighted averaging of raw data. As another example, the sequence can be combined by aligning the multiple instances of called sequence and obtaining a consensus sequence.

IX. Novel Nanopore Devices

Commercially available nanopore sequencing devices contain ordered arrays of nanopores that are operably linked to electrodes for sensing the electrical properties of the nanopore as a polynucleotide is translated through. For example, the MinION™ device (Oxford Nanopore Technologies) has 512 such nanopores, providing 512 different signal channels. Each nanopore is located in a microwell associated with its own electrode. However, not all the signal channels in a given device are necessarily operative.

Such, devices provide much less throughput than other high-throughput sequencing methods. For example, at 512 nanopores and an average read length of less than about 10 kb (for a typically fragmented nucleic acid sample), the MinION™ devices can provide an approximate maximum of $5 \times 10^6$ bases of sequence data per run. The density and number of nanopores in an ordered nanopore array device can be increased using traditional chip manufacturing methods such as spotting, lithography, electron beam irradiation, etc. However, due to the inherent limits of these methods with regard to feature size, there is a practical limit to the number of nanopores that can be obtained in an ordered nanopore array sequencing device.

Described herein are nanopore sequencing devices comprising a membrane containing randomly distributed nanopores. This can avoid the inherent limitations of traditional chip manufacturing techniques, allowing a dramatic increase in the number and density of nanopores in a device. This dramatic increase in nanopore density and number can provide a dramatic increase in sequence throughput. Provided herein is a nanopore sequencing device with at least $1 \times 10^9$ electrical sensors (electrodes), and at least $1 \times 10^9$ randomly, or pseudo-randomly, distributed nanopores. At least 10% of the electrodes in this device are operably linked to a single nanopore. Thus, the device provides at least $1 \times 10^8$ valid signal channels. Therefore, assuming an average read length of 10 kb the device can provide an approximate maximum of $(1 \times 10^8 * 10 \text{ kb}=) 1 \times 10^{12}$ bases of sequence data per run. Assuming the device provides an average read length of 10 kb, and the device is contacted with concatemer nucleic acids having an average of 10 copies of a target sequence, the device can provide an approximate maximum of $(1 \times 10^8 * 10 \text{ kb}/10 \text{ copies}=) 1 \times 10^{11}$ bases of high accuracy sequence data per run.

In one embodiment, the device comprising a membrane containing randomly or psuedo-randomly distributed nanopores contains a lipid membrane. Lipid membranes are fluidic by nature. Nanopores that transverse a lipid membrane can move around if not anchored or fixed in some manner. A plurality of nanopores can be loaded onto a lipid membrane and allowed to diffuse or distribute randomly within the membrane. The distribution pattern may change over time. To increase the fluidity of a membrane, one can apply cholesterol or other membrane modifiers into the lipid.

In some cases, after the nanopores are sufficiently distributed, they can be fixed. Nanopores can be fixed by a variety of methods. For example, the membrane (and nanopores distributed therein) can be cooled below a transition temperature. As another example, the membrane (and nanopores distributed therein) can be contacted with a cross-linking chemical. As another example, the membrane (and nanopores distributed therein) can be exposed to ultraviolet radiation to photo-crosslink the nanopores or membrane. As yet another example, the physical location of nanopores can be fixed by incorporating electrodes into the nanopore sequencing device to hinder the mobility of individual nanopores.

In some cases, the electrodes in the nanopore sequencing device are micro-scale electrodes. In some cases, the micro-scale electrodes are micropipettes (e.g., glass pipettes). In some cases, the electrode is a micropipette that has an open tip diameter of less than one micrometer. External micro-scale pipettes can be attached to, or sealed onto, the membrane in a manner similar to that used in a typical patch clamp setting. In some cases, the electrodes are randomly attached to the membrane. The diameter enclosed by the electrode tip can be in the micrometer range, typically containing one or zero nanopores.

In some cases, the interior of the pipette is filled with the same solution matching the ionic composition of a bath solution, in which the membrane is immersed. A wire (e.g., a chlorided silver wire) can be placed in contact with this solution to conduct electric current to the external recorder/amplifier. The micropipette can be pressed against a membrane and suction applied to assist in the formation of a high resistance seal between the glass and the membrane. A high resistance seal can electronically isolate the changes in one or more electronic properties from other noise or signals in the environment. A high resistance seal can also provide some mechanical stability to the device. For example, the seal can hinder the movement of, or immobilize, a nanopore contained therein.

In some cases, at least about $1 \times 10^3$, $1 \times 10^4$, $1 \times 10^5$, $1 \times 10^6$, $1 \times 10^7$, $1 \times 10^8$, $1 \times 10^9$, or $1 \times 10^{10}$ micro-scale electrodes may be applied to a membrane. The micro-scale electrodes can be applied in a fixed array fashion, or they can be randomly distributed. As the nanopores are randomly distributed across the membrane, a population of these electrodes will contain one nanopore within, and provide a valid signal channel, while others will not record any signal. In some cases, electrodes containing more than one, or zero, nanopores can be detected and ignored, inactivated, or disabled for use in sequencing. In some cases, electrodes containing only one nanopore are selected for signal detection or recordation.

X. Illustrative Example

A nucleic acid fragment containing a target sequence is ligated to an adaptor containing a non-target sync sequence. The nucleic acid fragment is circularized and amplified by rolling circle amplification. The resulting amplification product is a non-naturally occurring concatemer nucleic acid containing from 5 to 100 copies or more of the target sequence, each copy of the target sequence separated by a copy of the non-target sync sequence. The concatemer is contacted with a nanopore sequencing device and translated through the nanopore by application of a voltage potential. A dataset representing changes in current through the nanopore as nucleotides of the concatemer traverse the nanopore is recorded. The dataset is analyzed to identify areas corresponding to non-target sync sequence. The areas corresponding to non-target sync sequence are used to identify the portions of the dataset corresponding to the copies of the target sequence. The portions of the dataset corresponding to the copies of the target sequence are combined by averaging to obtain a consensus signal. The consensus signal is analyzed to determine the target sequence.

XI. Incorporation by Reference

References and citations to other documents, such as patents, patent applications, patent publications, journals, books, papers, and web contents throughout this disclosure are hereby incorporated herein by reference in their entirety for all purposes.

XII. Equivalents

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A multi-pass method of sequencing a target sequence using nanopore sequencing, the method comprising:

i) providing a non-naturally occurring concatemer nucleic acid molecule comprising monomeric units that comprise (a) the target sequence, and (b) a non-target sync sequence having a predetermined sequence,
wherein copies of the target sequence are separated by non-target sync sequences that demarcate a target sequence boundary,
wherein the concatemer comprises a plurality of copies of the target sequence and a plurality of copies of the sync sequence; and then ii) nanopore sequencing at least three copies of the target sequence in the concatemer, thereby obtaining a multi-pass sequence dataset, wherein the multi-pass sequence dataset comprises target sequence datasets for the at least three copies of the target sequence; and iii) using the multi-pass sequence dataset to determine the target sequence wherein the non-target sync sequences are used to align the target sequences in the multi-pass sequence dataset.

2. The method of claim 1, wherein the nanopore sequencing further comprises sequencing at least four sync sequences.

3. The method of claim 2, wherein all of the sync sequences are the same.

4. The method of claim 2, wherein the sync sequences are shorter than the target sequence.

5. The method of claim 1, wherein the multi-pass sequence has an accuracy of at least Q6.

6. The method of claim 1, wherein the concatemer comprises at least 5 copies, optionally at least 8 copies, of the target sequence.

7. The method of claim 1, wherein the concatemer comprises a calibration sequence.

8. The method of claim 1, wherein the providing the concatemer comprises circularizing a nucleic acid fragment comprising the target sequence to produce a circular nucleic acid; and using the circular nucleic acid as a template for rolling circle replication, thereby providing a concatemer.

9. The method of claim 7, wherein the nanopore sequencing in step (ii) comprises sequencing the calibration sequence, thereby obtaining calibration information, and further comprises using the calibration information to model base-calling for one or more nanopore channels.

10. The method of claim 9, wherein the concatemer contains one copy of the calibration sequence.

11. The method of claim 9, wherein the concatemer contains two copies of the calibration sequence.

12. The method of claim 9 wherein the concatemer comprises two different calibration sequences.

13. The method of claim 9 wherein the concatemer comprises no more than 3 copies of the calibration sequence.

14. The method of claim 9 wherein the calibration sequence(s) is not within a monomeric unit.

15. The method of claim 9, wherein step iii) comprises using the calibration information to optimize the base call model to the particular electrical and physical properties of the nanopore from which the calibration information is derived.

16. The method of claim 9 wherein the target sequence is genomic DNA or is complementary DNA transcribed from mRNA or rRNA.

17. The method of claim 9, wherein the concatemer nucleic acid molecule comprises 3-300 monomers and comprises a calibration sequence outside of the 3-300 monomers or comprises a pair of calibration sequences that flank the 3-300 monomers.

* * * * *